(12) United States Patent
Kawagoe et al.

(10) Patent No.: US 11,058,795 B2
(45) Date of Patent: Jul. 13, 2021

(54) SEMIPERMEABLE MEMBRANE AND METHOD OF MANUFACTURING THE SAME

(71) Applicant: KURARAY CO., LTD., Kurashiki (JP)

(72) Inventors: Masako Kawagoe, Chiyoda-ku (JP); Kiyofumi Enomoto, Kurashiki (JP)

(73) Assignee: KURARAY CO., LTD., Kurashiki (JP)

( * ) Notice: Subject to any disclaimer, the term of this patent is extended or adjusted under 35 U.S.C. 154(b) by 0 days.

(21) Appl. No.: 16/070,989

(22) PCT Filed: Jan. 19, 2017

(86) PCT No.: PCT/JP2017/001764
§ 371 (c)(1),
(2) Date: Jul. 18, 2018

(87) PCT Pub. No.: WO2017/126612
PCT Pub. Date: Jul. 27, 2017

(65) Prior Publication Data
US 2019/0015547 A1 Jan. 17, 2019

(30) Foreign Application Priority Data

Jan. 19, 2016 (JP) .............................. JP2016-007721

(51) Int. Cl.
*A61L 27/16* (2006.01)
*A61L 27/18* (2006.01)
(Continued)

(52) U.S. Cl.
CPC ................. *A61L 27/16* (2013.01); *A61F 2/02* (2013.01); *A61L 27/18* (2013.01); *A61L 27/20* (2013.01);
(Continued)

(58) Field of Classification Search
CPC .......... A61L 27/16; A61L 27/18; A61L 27/20; A61F 2/02; B01D 67/0016; B01D 71/10;
(Continued)

(56) References Cited

U.S. PATENT DOCUMENTS 4,839,055 A * 6/1989 Ishizaki .............. A61M 1/3472
210/321.84
4,968,733 A 11/1990 Müller et al.

FOREIGN PATENT DOCUMENTS

DE 10239658 A1 * 11/2003 .......... A61M 1/0236
JP 61-276561 A 12/1986
(Continued)

OTHER PUBLICATIONS

Naoya Kobayashi, et al., "Bioimplantable bioartificial pancreas embedded in the body," [online], Dec. 19, 2011, Japan Science and Technology Agency, [retrieved on Jan. 15, 2016], Internet <URL: http://www.jst.go.jp/chiiki/ikusei/seika/h22/h22_hiroshima01.pdf>, 5 pages (with English translation).
(Continued)

*Primary Examiner* — James C Goloboy
(74) *Attorney, Agent, or Firm* — Oblon, McClelland, Maier & Neustadt, L.L.P.

(57) ABSTRACT

The present disclosure relates to a semipermeable membrane. The present disclosure aims to provide a semipermeable membrane having tolerance against a decrease over time in substance permeability. The present disclosure provides a semipermeable membrane containing a resin. The permeation rate of albumin in the semipermeable membrane is no lower than 30%. The albumin adsorption amount obtained when the semipermeable membrane measuring 1 cm on each side is immersed in a 0.1% albumin solution for 90 minutes is no greater than 10 μg/cm². The water permeation amount obtained when water is sucked through the semipermeable membrane at a negative pressure of 3±0.2
(Continued)

kPa is expressed by no smaller than 1,000 L/(m² hour). The semipermeable membrane can isolate a cell from an external environment.

14 Claims, 1 Drawing Sheet

(51) Int. Cl.
| | |
|---|---|
| *B01D 71/76* | (2006.01) |
| *B01D 71/10* | (2006.01) |
| *B01D 71/50* | (2006.01) |
| *A61F 2/02* | (2006.01) |
| *B01D 71/68* | (2006.01) |
| *B01D 71/42* | (2006.01) |
| *B01D 71/56* | (2006.01) |
| *A61L 27/20* | (2006.01) |
| *B01D 67/00* | (2006.01) |
| *B01D 71/38* | (2006.01) |
| *B01D 71/26* | (2006.01) |

(52) U.S. Cl.
CPC ......... *B01D 67/0016* (2013.01); *B01D 71/10* (2013.01); *B01D 71/42* (2013.01); *B01D 71/50* (2013.01); *B01D 71/56* (2013.01); *B01D 71/68* (2013.01); *B01D 71/76* (2013.01); *B01D 71/26* (2013.01); *B01D 71/38* (2013.01)

(58) Field of Classification Search
CPC ........ B01D 71/26; B01D 71/38; B01D 71/42; B01D 71/50; B01D 71/56; B01D 71/68; B01D 71/76
See application file for complete search history.

(56) References Cited

FOREIGN PATENT DOCUMENTS

| | | |
|---|---|---|
| JP | 5-293344 A | 11/1993 |
| JP | 11-169693 A | 6/1999 |
| JP | 2001-299908 A | 10/2001 |
| JP | 2001-314736 A | 11/2001 |
| JP | 2003-10654 A | 1/2003 |
| JP | 2004-275718 A | 10/2004 |
| WO | WO 97/20885 A1 | 6/1997 |
| WO | WO 00/43115 A1 | 7/2000 |
| WO | WO 2010/002502 A2 | 1/2010 |
| WO | WO-2015118045 A1 * | 8/2015 ........... B01D 69/087 |

OTHER PUBLICATIONS

Shuhei Nakaji, et al., "Development of novel treatment of diabetes by implantable bioartificial pancreas," [online], Okayama University of Science, Liaison Office of OUS, [retrieved on Jan. 15, 2016], Internet <URL: http://www.ous.ac.jp/renkel/wp-content/uploads/2012/01/C-5.pdf>, 3 pages (with English translation).

Takeshi Yuasa, et al., "Neovascularization Induced Around an Artificial Device Implanted in the Abdomen by the Use of Gelatinized Fibroblast Grown Factor 2,", Cell Transplantation, vol. 18, 2009, pp. 683-688.

International Search Report dated Apr. 25, 2017 in PCT/JP2017/001764 filed Jan. 19, 2017.

Extended European Search Report dated Aug. 27, 2019, in Patent Application No. 17741489.3, 10 pages.

Wang, Z. et al., "Dissolution with EVOH in DMSO and preliminary characterization of EVOH membrane", ICAFPM 2011—Proceedings of 2011 International Conference on Advanced Fibers and Polymer Materials, XP009515073, Jan. 1, 2011, pp. 608-611.

De Lima, J. A. et al., "Porous polymer structures obtained via the TIPS process from EVOH/PMMA/DMF solutions", Journal of Membrane Science, XP026601999, vol. 344, No. 1-2, Nov. 15, 2009, pp. 237-243.

Notice of Reasons for Refusal dated Jan. 19, 2021 in Japanese Patent Application No. 2017-562893 (with English machine translation), 12 pages.

Shuhel Takemura, et al., "New Aspects of the Complement System," Jpn. J. Clin. Immun., vol. 11, No. 2, 1988, pp. 93-98 (with English machine translation).

Manabu Senoo, "Biofunctional membrane," BME, vol. 1, No. 2, 1987, pp. 99-107 (with English machine translation).

* cited by examiner

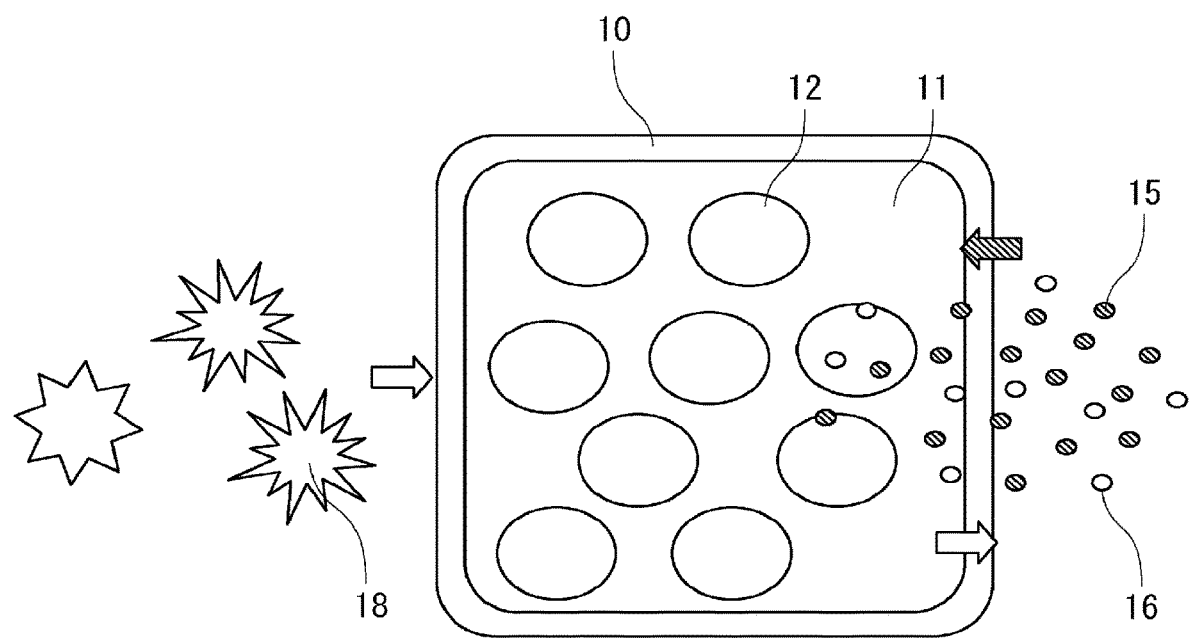

SEMIPERMEABLE MEMBRANE AND METHOD OF MANUFACTURING THE SAME

TECHNICAL FIELD

The present disclosure relates to a semipermeable membrane and a method of manufacturing the semipermeable membrane.

BACKGROUND ART

In recent years, bioartificial organs produced by combining artificial materials and cells are being studied. Bioartificial organs are devices intended to prevent or treat patients' diseases. Bioartificial organs contain thereinside cells and biological tissues to thus provide metabolic functions necessary for the patients. Specifically, bioartificial organs provide the patients with biologically active factors that control the metabolic functions of the cells and the biological tissues. Examples of the biologically active factors include hormones and proteins. Recent studies on bioartificial organs are aiming to exploit the advantages of each of the artificial materials and the cells.

With a bioartificial organ, the type of cells constituting the bioartificial organ can be selected in accordance with the type of disease to be treated. Examples of the bioartificial organs include a bioartificial pancreatic islet. A bioartificial pancreatic islet contains insulin-secreting cells, a cell group including insulin-secreting cells, or the like. Examples of the cell group include a pancreatic islet. A bioartificial pancreatic islet can be used to supply an insulin hormone to a patient who has difficulty in controlling or is unable to control the blood sugar level. Thus, the blood sugar level of such a patient can be corrected.

Another bioartificial organ produces a blood coagulation factor as a biologically active factor. Such a bioartificial organ includes thereinside hepatic cells that produce a blood coagulation factor. Examples of the blood coagulation factor include factor VIII and factor XI. Such a bioartificial organ is being used to treat a hemophilic patient with a blood coagulation disorder attributable to the deficiency of the aforementioned blood coagulation factors.

Another bioartificial organ produces a growth hormone. Such a bioartificial organ includes human growth hormone (hGH) secreting cells. Such a bioartificial organ is being used to treat pituitary dwarfism attributable to the deficiency of growth hormone secretion, for example.

Another bioartificial organ contains cells that secrete a parathyroid hormone. Such a bioartificial organ can be used to treat hypoparathyroidism. Another bioartificial organ contains cells that secrete erythropoietin. Such a bioartificial organ can be used to treat anemia.

A bioartificial organ is a device to be implanted into a patient's body. A bioartificial organ implant has some advantages over a living organ transplant. On one hand, a living organ transplant may not be suitable for retaining the effect over an extended period of time. This is because, in a living organ transplant, the transplanted cells are rejected in the patient's body by the protective mechanism of the organism. Examples of the protective mechanism include an acute rejection reaction that occurs primarily within half a year of the transplant and a chronic rejection reaction that progresses in several years thereafter. Such a problem arises in an allogeneic transplant as well.

The protective mechanism of an organism functions by an antibody protein and a complement protein involved in humoral immunity and by cell-mediated immunity. In a living organ transplant, it is difficult to isolate the transplanted cells from the protective mechanism of the organism. In contrast, a bioartificial organ includes an immunoisolation membrane of an artificial material. An immunoisolation membrane can protect the cells composing the bioartificial organ from humoral immunity and cell-mediated immunity.

In addition, a mismatch in demand and supply occurs between a donor and a recipient in a living organ transplant. This is inevitable in order to prevent a rejection reaction. As compared to a living organ transplant, the propriety of an implant is not influenced much by the issue of a mismatch in a bioartificial organ implant. This is because the immunoisolation membrane can protect the cells composing the bioartificial organ from the protective mechanism of the organism and a rejection reaction can thus be prevented more easily. In addition, in a bioartificial organ implant, no immunosuppressant is required, or only a smaller amount of immunosuppressant is prescribed than in a living organ transplant.

In the study of bioartificial organs, an immunoisolation membrane having permeation selectivity has been searched for with respect to polymers, such as proteins, involved in humoral immunity. An immunoisolation membrane can isolate the cells composing the bioartificial organ from humoral immunity and cell-mediated immunity by the permeation selectivity.

Even bioartificial organs suffer from a problem that makes it difficult to retain the effect for an extended period of time. This is due to clogging produced at a permeating portion of the immunoisolation membrane. Clogging at the permeating portion occurs due to poor biological compatibility of the artificial material itself. In other words, clogging at the permeating portion occurs as the artificial material is covered by a fibrous capsule.

There are bioartificial organs of various forms, including one of a microcapsule type. In a bioartificial organ of a microcapsule type, cells are encapsulated by an artificial material. Examples of such artificial materials to be used include a membrane-type or gel-type macromolecular polymer. A macromolecular polymer, serving as an immunoisolation membrane, protects the cells contained in the microcapsule from the protective mechanism of the organism. Furthermore, the molecular permeability can be controlled by making a certain arrangement in the structure of the immunoisolation membrane. The molecular permeability needs to be controlled in order for the bioartificial organ to supply the organism with hormones and proteins secreted from the cells or to take in nutrients necessary for the cells to stay alive.

Patent Literature 1 discloses a bag for a cell implant as one embodiment of a form of an immunoisolation membrane. Such a bag is formed of a polyethylene terephthalate (PET) mesh. Such a bag can be used to fabricate a bioartificial pancreas.

Patent Literature 2 discloses a module for a bioartificial pancreas to be worn externally on a body. A hollow fiber composed of a polymer semipermeable membrane is used in the stated module. The polymer semipermeable membrane is composed of an ethylene-vinylalcohol-based copolymer. The membrane thickness and the pore size of the hollow fiber are substantially equal to those of a typical dialysis membrane for artificial kidney, a blood plasma component separation membrane, or a blood plasma separation membrane. By introducing blood into the hollow fiber, the substance in the blood is fed to the cells composing the bioartificial pancreas through the polymer semipermeable membrane. In addition, substances secreted from the cells can be fed into the body from the blood passing through the hollow fiber. Non Patent Literatures 1 and 2 disclose a bioartificial pancreas (BAP) fabricated by combining a device composed of the above-described semipermeable membrane of a body-implantable type and blood-sugar-responsive insulin-secreting cells.

Patent Literature 3 discloses a hollow fiber membrane composed of a polymer semipermeable membrane having high permeability and high fractionation capability. This hollow fiber membrane is used for medical purposes, such as hemodialysis and blood plasma separation.

CITATION LIST

Patent Literature

Patent Literature 1: Japanese Unexamined Patent Application Publication No. 2001-299908
Patent Literature 2: Japanese Unexamined Patent Application Publication No. 2004-275718
Patent Literature 3: Japanese Unexamined Patent Application Publication No. 2001-314736

Non Patent Literature

Non Patent Literature 1: Kobayashi, Naoya, and one other, "body-implantable bioartificial pancreas," [online], Dec. 19, 2011, Japan Science and Technology Agency, [retrieved on Jan. 15, 2016], Internet <URL: http://www.jst.go.jp/chiiki/ikusei/seika/h22/h22 hiroshima01.pdf>
Non Patent Literature 2: Nakaji, Shuhei, and eight others, "development of novel treatment of diabetes with implantable bioartificial pancreas," [online], Okayama University of Science, Liaison Office of OUS, [retrieved on Jan. 15, 2016], Internet <URL: http://www.ous.ac.jp/renkei/wp-content/uploads/2012/01/C-5.pdf>

SUMMARY OF INVENTION

Technical Problem

In the semipermeable membrane of the bioartificial organ disclosed in Patent Literature 2 or in the polymer semipermeable membrane composing the hollow fiber membrane disclosed in Patent Literature 3, fine pores are provided in the surface thereof. Such pores provide the membrane with permeability. However, there is a problem in that the substance permeability of the semipermeable membrane decreases over time after the implant. The decrease in the substance permeability of the semipermeable membrane causes the function of the cells in the bioartificial organ to deteriorate. Accordingly, the function of the bioartificial organ deteriorates.

The present disclosure is directed to providing a semipermeable membrane for isolating cells from an external environment. The present disclosure aims to provide a semipermeable membrane having high substance permeability as well as tolerance against a decrease over time in the substance permeability of the semipermeable membrane within an organism.

Solution to Problem

[1] A semipermeable membrane comprises a resin. In the semipermeable membrane, a permeation rate of albumin is no lower than 30%, and an albumin adsorption amount obtained when the semipermeable membrane measuring 1 cm on each side is immersed in a 0.1% albumin solution for 90 minutes is no greater than 10 μg/cm$^2$.

[2] The semipermeable membrane according to [1], in which a water permeation amount obtained when water is sucked through the semipermeable membrane at a negative pressure of 3±0.2 kPa is expressed by no smaller than 1,000 L/(m$^2$·hour).

[3] The semipermeable membrane according to [1] or [2], in which a decrease in a complement level (CH50) in a serum by the semipermeable membrane when the semipermeable membrane and the serum are brought into contact is no more than 25%.

[4] The semipermeable membrane according to any one of [1] to [3], in which an increase in an activity of a complement in a serum by the semipermeable membrane when the semipermeable membrane and the serum are brought into contact is no more than 30%, and the increase in the activity is calculated on the basis of an amount of one or more complements among C1, C2, C3, C4, C5, C6, C7, C8, and C9, an amount of a protein produced as the complements are degraded, and a measured amount of one or more of complexes of the complements.

[5] The semipermeable membrane according to any one of [1] to [4], in which the semipermeable membrane has a thickness of no less than 50 μm nor more than 200 μm.

[6] The semipermeable membrane according to any one of [1] to [5], in which a mean pore size in at least one surface is no less than 0.1 μm nor more than 3 μm.

[7] The semipermeable membrane according to any one of [1] to [6], in which the resin is an ethylene-vinylalcohol-based copolymer, and the semipermeable membrane contains the ethylene-vinylalcohol-based copolymer at no less than 50 mass %.

[8] The semipermeable membrane according to any one of [1] to [7], in which the semipermeable membrane is for isolating a cell from an external environment.

[9] A bag consisting of the semipermeable membrane according to any one of [1] to [8].

[10] A method of manufacturing a semipermeable membrane, in which a stock solution for membrane manufacturing is obtained by mixing components to result in a mass ratio of from 7.5 mass % to 25 mass % of a resin, from 55 mass % to 87.5 mass % of a solvent, and from 5 mass % to 20 mass % of an additive; the resin is at least one of an ethylene-vinylalcohol-based copolymer, a polysulfone-based polymer, a polyacrylonitrile-based polymer, a cellulose-based polymer, a polyamide-based polymer, and a polycarbonate-based polymer; and the additive is a water-soluble polymer.

[11] The method of manufacturing a semipermeable membrane according to [10], in which the stock solution for membrane manufacturing is obtained by heating and dissolving the components in a range of from 50° C. to 120° C., the stock solution for membrane manufacturing is retained at 20° C. to 95° C., and the stock solution for membrane manufacturing is then coagulated at a temperature of 20° C. to 80° C.

[12] The method of manufacturing a semipermeable membrane according to [11], in which the stock solution for membrane manufacturing is coagulated in a coagulation bath.

Advantageous Effects of Invention

The present disclosure can provide a semipermeable membrane having high substance permeability as well as tolerance against a decrease over time in the substance permeability of the semipermeable membrane within an organism. Accordingly, the present disclosure can provide a semipermeable membrane having high biological compatibility.

BRIEF DESCRIPTION OF DRAWINGS

FIG. 1 is a schematic diagram of a bag composed of a semipermeable membrane.

DESCRIPTION OF EMBODIMENTS

The term "cell" as used in the present specification includes, but is not limited to, an adherent cell and a suspension cell. An adherent cell refers to a cell that grows by adhering onto a carrier in cell culture. A suspension cell refers to a cell that basically requires no adherence onto a carrier in cell growth. A suspension cell includes a cell capable of weakly adhering onto a carrier.

Examples of the adherent cell include, but are not limited to, an osteoblast, a chondrocyte, a hematopoietic cell, an epithelial cell (e.g., mammary epithelial cell), an endothelial cell (e.g., vascular endothelial cell), an epidermal cell, a fibroblast, a mesenchymal-derived cell, a cardiomyocyte, a myoblast, a smooth muscle cell, an organism-derived skeletal muscle cell, a human tumor cell, a fibrocyte, an EB virus mutant cell, a hepatic cell, a renal cell, a bone marrow cell, a macrophage, a hepatocyte, a small intestine cell, a mammary gland cell, a salivary gland cell, a thyroid cell, and a skin cell.

Examples of the suspension cell include, but are not limited to, a T cell, a B cell, a killer cell, a lymphocyte, a lymphoblast cell, and a pancreatic β cell.

The aforementioned cells may be coagulated together or differentiated. Coagulated cells may have a function as an organ. Cells may be those that have just been sampled from an organism or those that are cultured. Cells sampled from an organism may form an organ.

[Resin]

A semipermeable membrane according to the present disclosure can be fabricated, for example, by dissolving at least one or more types of resins in a solvent and coagulating the dissolved resins. Such resins are not particularly limited. Examples of such resins that can be used include an ethylene-vinylalcohol-based copolymer, a polysulfone-based polymer, a polyacrylonitrile-based polymer, a cellulose-based polymer such as cellulose acetate, a polyamide-based polymer, and a polycarbonate-based polymer. The weight-average molecular weight of these resins is preferably no less than 10,000.

The content of the resins in the semipermeable membrane according to the present disclosure is preferably no less than 50 mass %, more preferably no less than 80 mass %, or even more preferably no less than 90 mass %. Aside from the resins, an additive or a solvent used to manufacture the membrane may remain in the semipermeable membrane. The content of such, however, is preferably no more than 50 mass %, more preferably no more than 20 mass %, or even more preferably no more than 10 mass %.

When the semipermeable membrane according to the present disclosure is used for a medical purpose such as a bioartificial organ, it is preferable to use an ethylene-vinylalcohol-based copolymer or a polysulfone-based polymer as the resin. Such resins are less likely to activate a complement and excel in the biological compatibility and the chemical stability. In addition, these resins are less likely to biodegrade in an organism and produce less eluate.

The ethylene-vinylalcohol-based copolymer used in the present disclosure may be any one of a random polymer, a block polymer, and a graft polymer. The content by percentage of an ethylene structural unit in the ethylene-vinylalcohol-based copolymer is preferably no less than 10 mol % nor more than 90 mol %. Setting the content by percentage of the ethylene structural unit to no less than 10 mol % makes it possible to suppress complement activation by the semipermeable membrane. In order to further suppress the complement activation, the content by percentage of the ethylene structural unit is preferably no less than 30 mol %. Setting the content by percentage of the ethylene structural unit to no more than 90 mol % makes it possible to suppress a decrease in the flexibility of the semipermeable membrane. In order to further suppress the decrease in the flexibility, the content by percentage of the ethylene structural unit is preferably no more than 60 mol %. The degree of saponification of the ethylene-vinylalcohol-based copolymer is preferably no lower than 95 mol %.

The ethylene-vinylalcohol-based copolymer is composed primarily of an ethylene structural unit and a vinylalcohol structural unit. The ethylene-vinylalcohol-based copolymer may include another monomeric structural unit as a structural unit. The ethylene-vinylalcohol-based copolymer need not include any other monomeric structural unit. Examples of other monomers include methacrylic acid, vinyl chloride, methyl methacrylate, and acrylonitrile. The content by percentage of another monomeric structural unit in the ethylene-vinylalcohol-based copolymer can be adjusted as appropriate within a range that does not hinder the spirit of the present disclosure. The content by percentage of such is preferably no more than 15 mol %.

[Membrane Thickness]

The semipermeable membrane according to the present disclosure has a thickness of preferably no less than 50 μm nor more than 200 μm. Setting the thickness to no less than 50 μm makes it possible to increase the strength of the semipermeable membrane. Setting the thickness to no more than 200 μm makes it possible to provide a semipermeable membrane of which the permeation rate of proteins such as albumin or the water permeation amount is adjusted with ease to a desired range.

[Pore Size]

The semipermeable membrane according to the present disclosure is a porous membrane having a plurality of fine pores provided therein. The mean pore size of such pores is preferably no smaller than 0.1 μm nor greater than 3 μm, more preferably no smaller than 0.3 μm nor greater than 3 μm, or even more preferably no smaller than 0.5 μm nor greater than 2 μm. Setting such lower limits in the mean pore size makes it possible to increase the permeation rate of proteins or the water permeation amount. In addition, setting such upper limits in the mean pore size makes it possible to suppress permeation of external cells or the like. The pore sizes of the pores have a predetermined distribution in the semipermeable membrane. At this point, it is preferable that no pore having a pore size of 20 μm or greater be present in the surface of the semipermeable membrane, in order to prevent permeation of external cells or the like.

[Membrane Manufacturing]

A method of manufacturing the semipermeable membrane according to the present disclosure is not particularly limited. For example, the semipermeable membrane can be obtained by fabricating a nonporous membrane through a well-known method and making pores in the nonporous membrane through drilling. In addition, the semipermeable membrane can be manufactured, for example, through the following method.

First, a resin, a solvent, and an additive are mixed together, and the mixture is heated and dissolved in a range of from 50° C. to 120° C. to obtain a stock solution for membrane manufacturing in which the components are mixed together. The stock solution for membrane manufacturing is retained in a temperature range of preferably from 20° C. to 95° C. or more preferably from 50° C. to 90° C. Thereafter, the stock solution for membrane manufacturing is coagulated at a temperature of from 20° C. to 80° C. to form a membrane.

In one example, a resin, an additive, and a solvent are mixed together, and the mixture is heated and dissolved at a temperature of preferably from 50° C. to 120° C. or more preferably from 50° C. to 80° C. to obtain a stock solution for membrane manufacturing. The stock solution for membrane manufacturing further heated to a temperature of from 20° C. to 95° C. or more preferably from 20° C. to 80° C. is applied onto a plate-shaped forming device. The stock solution for membrane manufacturing on the forming device is coagulated in a coagulation bath of from 20° C. to 80° C. or more preferably from 20° C. to 60° C., and a semipermeable membrane primarily composed of the resin is obtained as the additive and the solvent are diffused in the coagulation bath. Thereafter, a purifying process and a drying process can be performed as appropriate.

With regard to the mass ratio in the stock solution for membrane manufacturing, the proportion of the resin is preferably from 7.5 mass % to 25 mass % or preferably from 10 mass % to 20 mass %. The proportion of the solvent is preferably from 55 mass % to 87.5 mass % or preferably from 60 mass % to 80 mass %. The proportion of the additive is preferably from 5 mass % to 20 mass %. In order to facilitate the formation of the membrane, it is preferable that the proportion of the additive be lower than the proportion of the resin.

With regard to the manufacturing of the semipermeable membrane according to the present disclosure, the disclosure of Japanese Unexamined Patent Application Publication No. 2001-314736, or Patent Literature 3, is incorporated herein in its entirety.

[Stock Solution for Membrane Manufacturing]

The viscosity of the stock solution for membrane manufacturing at 30° C. is preferably no lower than 1,000 mPa·s nor higher than 20,000 mPa·s or more preferably no lower than 1,000 mPa·s nor higher than 10,000 mPa·s.

When the viscosity of the stock solution for membrane manufacturing is lower than 1,000 mPa·s or higher than 20,000 mPa·s, it is difficult to adjust the coagulation time of the stock solution for membrane manufacturing, and the membrane manufacturing can be difficult. In addition, the membrane may be easily damaged after the stock solution for membrane manufacturing is coagulated.

[Measuring Viscosity of Stock Solution for Membrane Manufacturing]

The viscosity of the stock solution for membrane manufacturing at 30° C. can be measured with the use of a BL viscometer or a BH viscometer under the conditions in which the number of rotations of the rotor is 6 rpm and the temperature is 30° C.

[Solvent for Membrane Manufacturing]

The solvent composing the stock solution for membrane manufacturing is not particularly limited, and any good solvent for a resin to be used in the membrane manufacturing can be used. Examples of such include dimethyl sulfoxide (DMSO), N,N-dimethylformamide (DMF), dimethylacetamide (DMAc), or the like or a mixed solvent having the above as components. From the viewpoint of membrane manufacturing performance and low toxicity, dimethyl sulfoxide (DMSO) is preferable among the above.

[Additive for Membrane Manufacturing]

The additive composing the stock solution for membrane manufacturing is preferably a water-soluble polymer. For example, what is generally referred to as a surfactant can be used as an additive. The surfactant is preferably a macromolecular surfactant. Adjusting the type or the amount of the additive makes it possible to adjust the mean pore size of the pores in the semipermeable membrane. In addition, the viscosity of the stock solution for membrane manufacturing can be adjusted. Furthermore, the land surface temperature (LST) of the stock solution for membrane manufacturing can be adjusted.

A macromolecular surfactant refers to a surfactant having a molecular weight of no less than any one of 1,000, 2,000, 3,000, 4,000, 5,000, 6,000, 7,000, 8,000, and 9,000. The surface activity function may be any one of a nonionic one, an anionic one, and a cationic one. A nonionic macromolecular surfactant is preferable among the above.

Examples of the nonionic macromolecular surfactants include the following: polymers such as polyethylene glycol, polyethylene oxide, polypropylene glycol, and polypropylene oxide; diblock copolymers or random copolymers such as polyethylene glycol-polypropylene glycol, polyethylene glycol-polytetramethylene glycol, polyethylene glycol-polybutylene glycol, and polyethylene glycol-polypentylene glycol; triblock copolymers such as polyethylene glycol-polypropylene glycol-polyethylene glycol, polyethylene glycol-polytetramethylene glycol-polyethylene glycol, polyethylene glycol-polybutylene glycol-polyethylene glycol, and polyethylene glycol-polypentylene glycol-polyethylene glycol; polypropylene glycol-sulfuric acid ester sodium salt, polytetramethylene glycol-sulfuric acid ester sodium salt, polybutylene glycol-sulfuric acid ester sodium salt, and polypentylene glycol-sulfuric acid ester sodium salt; and polyethylene glycol-polypropylene glycol-alkyl ether.

Aside from the above that are generally referred to as surfactants, a water-soluble polymer can be used as an additive. For example, other examples include polysaccharides such as various well-known vinylalcohol-based polymers, starch, carboxymethyl cellulose, methyl cellulose, hydroxymethyl cellulose, hydroxyethyl cellulose, hydroxypropyl cellulose, and dextran.

[Activation of Complement]

The semipermeable membrane according to the present disclosure contains a resin. It is preferable that the surface of the semipermeable membrane be less likely to activate a complement in a serum. Whether the surface of the semipermeable membrane is less likely to activate the complement is expressed on the basis of the following evaluation methods.

<Method A: Evaluation Based on Measurement of Serum Complement Level (CH50)>

The semipermeable membrane is brought into contact with a fresh human serum. At this point, if the rate of decrease of the serum complement level (CH50) is no higher than 25%, the surface of the semipermeable membrane is evaluated to be less likely to activate a complement. The serum complement level is proportional to the total amount of complements C1, C2, C3, C4, C5, C6, C7, C8, and C9 remaining without being activated. The degree of activation of the complement can be evaluated on the basis of the serum complement level.

<Method B: Evaluation Based on Measurement of Activity of Individual Complements>

A complement in blood is usually present as an inactive enzyme precursor. An enzyme precursor is activated upon being stimulated by a foreign substance entering the body. The enzyme precursor is partially degraded upon activation and produces a partially degraded product. The partially degraded product is eliminated or forms a complex. Therefore, when the semipermeable membrane behaves as a foreign substance, the surface of the semipermeable membrane activates the complement. The evaluation can be made through the following evaluation method.

The semipermeable membrane is brought into contact with a fresh human serum. At this point, if the activation rate of the complement in the serum by the semipermeable membrane is no higher than 30%, the surface of the semipermeable membrane is evaluated to be less likely to activate a complement.

In one embodiment, an increase in the activity is calculated on the basis of the measurement of the amount of each complement in the fresh human serum brought into contact with the membrane. The complements to be measured are preferably one or more complements among C1, C2, C3, C4, C5, C6, C7, C8, and C9 or more preferably one or more complements of C3 and C4.

In one embodiment, an increase in the activity is calculated on the basis of the measurement of the amount of proteins (partially degraded product) produced as the aforementioned complements are degraded.

The proteins (partially degraded product) to be eliminated from the complements to be measured are preferably one or more proteins among C1r, C1q, C2b, C3a, C4a, and C5a, and the proteins to be eliminated from the complements are more preferably one or more proteins of C3a and C5a. C3a and C5a have functions of attracting an inflammatory leucocyte. In particular, C3a can be used effectively as an index of an onset of the activation of a complement system.

In one embodiment, an increase in the activity is calculated on the basis of the measurement of the amount of the complex in the aforementioned complement. The complex to be measured is preferably formed as the complements are activated and are thus be bonded together. The complex is preferably SC5b-9. SC5b-9 is an end product of a complement system activation reaction.

An example of a technique for quantitating an increase in the activity of the complement is illustrated below. To be more specific, the increase can be quantitated by the method described later in the examples.

First, a semipermeable membrane of a predetermined size is immersed in a fresh human serum of a predetermined amount. The volume of the serum per 1 cm$^2$ of the surface area of the semipermeable membrane is set to 1 mL. Here, the surface area inside the membrane produced by the pores may be ignored. This applies similarly hereinafter. The semipermeable membrane and the serum are incubated for 90 minutes at 37° C. while being stirred. The inner surface of a vessel for incubation is preferably blocked in advance with albumin. As a reference, a fresh human serum in which no semipermeable membrane is immersed (negative control) is also prepared. In addition, a fresh human serum to which zymosan of a predetermined amount, in place of the semipermeable membrane, is added (positive control) is also prepared. These are incubated for 90 minutes at 37° C. while being stirred.

After the incubation, disodium ethylenediaminetetraacetate (EDTA) serving as an activation reaction stopper is added to each fresh human serum to result in 10 mM. After the reaction stops, the amount of complement in the serum is measured. Here, the amount of complement in the serum may be the amount of proteins produced as the complement is degraded. The measurement can be carried out through an ELIZA technique. The amount (mass) of complement in the serum in which the semipermeable membrane has been immersed is designated by X. The amount (mass) of complement in the serum in which no semipermeable membrane has been immersed is designated by Xmin. The amount (mass) of complement in the serum to which zymosan has been added is designated by Xmax. The activation rate is calculated in accordance with the following formula.

Activation rate (%)={(X−Xmin)/(Xmax−Xmin)}×100

[Adsorptivity of Protein (Albumin)]

The surface of the semipermeable membrane according to the present disclosure is preferably less likely to adsorb proteins. Whether the surface of the semipermeable membrane is less likely to adsorb proteins can be evaluated on the basis of the following evaluation method in which albumin is used.

In the evaluation method in which albumin is used, first, a semipermeable membrane measuring 1 cm on each side is immersed in a 0.1% (1 mg/mL) human albumin solution for 90 minutes. At this point, if the amount of albumin adsorbed onto the semipermeable membrane is no more than 10 µg/cm$^2$, the surface of the semipermeable membrane is evaluated to be less likely to adsorb proteins. It is more preferable that the amount of adsorbed albumin be no more than any one of the values of 9, 8, 7, 6, 5, 4, 3, 2, and 1 µg/cm$^2$. The stated amount of adsorbed albumin can be adjusted by selecting the resin to be used to fabricate the semipermeable membrane. When the surface of the semipermeable membrane is less likely to adsorb proteins, a decrease over time in the substance permeability of the semipermeable membrane can be suppressed, and the biological compatibility can be evaluated to be high.

[Water Permeability]

The semipermeable membrane according to the present disclosure has high water permeability. The water permeability of the semipermeable membrane is evaluated by the amount of permeated water {L/(m$^2$·hour)} per unit area of the semipermeable membrane and per unit time when distilled water of 25° C. is sucked through the semipermeable membrane at a negative pressure of 3±0.2 kPa. If such an amount of permeated water is no less than 1,000 {L/(m$^2$·hour)}, the water permeability of the semipermeable membrane is evaluated to be high. Such an amount of permeated water is preferably no less than 2,000 {L/(m$^2$·hour)}. In addition, such an amount of permeated water is preferably no more than 20,000 {L/(m$^2$·hour)}, more preferably no more than 15,000 {L/(m$^2$·hour)}, or particularly preferably no more than 10,000 {L/(m$^2$·hour)}.

[Permeability of Substance (Albumin)]

The permeation rate of albumin in the semipermeable membrane according to the present disclosure is no lower than 30%, preferably no lower than 40%, or more preferably no lower than 50%. In addition, the permeation rate of albumin in the semipermeable membrane is preferably no higher than 90% or more preferably no higher than 80%. In the present embodiment, the permeation rate of albumin is used as an index of the substance permeability of the semipermeable membrane. Thus, the permeability of various proteins other than albumin can also be evaluated indirectly. In addition, the permeability of various amino acids such as glutamine, glucose, hormones, vitamins, and so on can also be evaluated indirectly. It is desirable that these substances permeate through the semipermeable membrane according to the present disclosure. The permeation rate of albumin can be measured through the following method.

A semipermeable membrane of a predetermined size is folded into two, and two sides of the folded piece are fused and bonded to fabricate a bag-like member with one side remaining unbonded. A predetermined amount of human albumin solution is injected into such a bag-like member, and the unbonded side of the bag-like member is fused and bonded to achieve sealing. Thus, a bag is formed from the bag-like member. A predetermined volume of the bag containing the human albumin solution is immersed in a predetermined amount of Hanks' buffer solution present, for example, in a 15-mL tube, or for example, in 10 mL of Hanks' buffer solution. The tube is shaken for 30 minutes at 37° C. After 30 minutes, the Hanks' buffer solution outside the bag is sampled. The concentration of albumin in the sampled Hanks' buffer solution is measured through an ELISA technique. The measurement through the ELISA technique may be carried out with the use of Human Albumin ELISA Quantitation Set (Bethyl Laboratories, Inc.). The permeation rate can be calculated through the following formula. The amount (mass) of permeated albumin transferred to the Hanks' buffer solution from the inside of the bag is designated by $X_n$. The amount (mass) of albumin in the same quantity as the quantity injected into the bag is designated by $X_{max}$.

Permeation rate (%)=$X_n/X_{max}\times 100$

Use

The semipermeable membrane according to the present disclosure can be used to isolate cells from an external environment. FIG. 1 illustrates one embodiment of a bag formed of a semipermeable membrane 10 according to the present disclosure. The bag contains a base material 11 for fixing cells inside the bag and desired cells 12. The cells 12 are sealed by the bag. Here, the bag is a member having a region closed by the semipermeable membrane provided therein. The bag can be fabricated, for example, through the method described in the section titled [Permeability of Substance (Albumin)]. In addition, the bag may be fabricated with the use of a plurality of semipermeable membranes.

The semipermeable membrane 10 allows nutrients 15 necessary for the cells 12 to permeate therethrough. The nutrients are, for example, an amino acid, a substance adsorbed onto albumin, or the like. The nutrients 15 move into the bag from the external environment. The semipermeable membrane 10 allows secreted substances 16 from the cells 12 to permeate therethrough. The secreted substances 16 move toward the external environment from the bag. The base material 11 suppresses coagulation of the cells and also uniformly disperses the cells inside the bag. In addition, the base material 11 suppresses humoral immunity. Examples of the base material 11 include a nonwoven fabric, a sheet, a gel or the like providing footing for the cells and can be fabricated with a material having good biological compatibility or with a biodegradable material.

Effect

The inventors have found the following issues with existing body-implantable bioartificial organs. Specifically, when a bag with cells sealed therein and the cells sealed in the bag are implanted as a bioartificial organ into an organism, proteins in the organism adhere onto the surface of the bag. In addition, cells adhere onto the surface with the proteins serving as footing, and a layer of cells is formed on the surface of the bag. Thus, the substance permeability of the bag decreases. The decrease in the substance permeability not only suppresses a release of substances secreted by the cells in the bag but also prevents the cells in the bag from receiving sufficient nutrients from the external environment. Accordingly, it is difficult to retain the function of the bioartificial organ over an extended period of time.

As illustrated in FIG. 1, the semipermeable membrane 10 constituting the bag has pores that are large enough to allow the nutrients 15 and the secreted substances 16 to permeate therethrough but does not allow external cells such as leucocytes 18 including a macrophage to permeate therethrough. Therefore, while the entry of the leucocytes 18 into the bag is being prevented, the diffusion of the nutrients 15 and the secreted substances 16 is facilitated.

In addition, the surface of the bag is less likely to activate a complement, and thus the external cells such as the leucocytes 18 are less likely to adhere onto the semipermeable membrane 10. In addition, the surface of the bag is less likely to adsorb proteins. Accordingly, a layer of cells is less likely to be formed on the surface of the bag. Thus, a decrease over time in the substance permeability of the bag inside the organism can be suppressed. Therefore, the semipermeable membrane 10 is effective in retaining the function of the bioartificial organ over an extended period of time.

The semipermeable membrane according to the present disclosure can be used as a variety of members, aside from the bag described above. For example, the semipermeable membrane can be processed into a cylindrical member formed of one semipermeable membrane or two or more semipermeable membranes. In addition, the semipermeable membrane can be processed into a bag-like member with only one open side formed of one semipermeable membrane or two or more semipermeable membranes. In addition, a new member can be obtained by combining a member made of the semipermeable membrane with another member. In addition, the semipermeable membrane may be subjected to surface treatment in accordance with the intended use. The semipermeable membrane according to the present disclosure and various members made of the semipermeable membrane can be widely used in medical purposes other than the bioartificial organs and in drug development research purposes or the like.

Modifications of Embodiments

It is to be noted that the present disclosure is not limited to the embodiments described above, and modifications can be made as appropriate within the scope that does not depart from the technical spirit.

EXAMPLES

Hereinafter, the present disclosure will be described in further detail through examples, but the present disclosure is not limited in any way by these examples. It is to be noted that the parts and the percentages indicate the parts by mass and the mass percentages in the following examples and comparative examples, unless specifically indicated otherwise.

[Fabrication of Semipermeable Membrane]

In each of the examples and the comparative examples, a semipermeable membrane is fabricated basically through the method of Example 1 illustrated below. Semipermeable membranes (porous membranes) having different pore sizes and different inner structures can be obtained by varying the composition of the stock solution for membrane manufacturing and the composition of the coagulation solution. Features that are to be modified from those of Example 1 in each of the examples and the comparative examples will be described later.

1. The stock solution for membrane manufacturing was prepared. All of the following materials were placed into a pressure-resistant test tube. The materials weighed 12 g in total. The materials were, as a resin, an ethylene-vinylalcohol-based copolymer (manufactured by KURARAY CO., LTD., Kuraray EVAL (registered trademark) G110B, the content by percentage of an ethylene structural unit was 47 mol %, the degree of saponification was 98 mol %, EVOH-1 in the present specification), as a solvent, dimethyl sulfoxide (DMSO), and as an additive, polyethylene oxide (PEO, the molecular weight was approximately 60,000); and the mass ratio of the above was 15:75:10. The pressure-resistant test tube was plugged, and the materials were sealed therein. The test tube was heated by a hot-air drier that supplies hot air of 100° C., and the temperature inside the test tube was brought to 90° C. The temperature inside the test tube was retained at 90° C. for three days while the test tube was shaken, and the stock solution for membrane manufacturing was obtained.

2. The hot-air drier was adjusted to adjust the temperature of the stock solution for membrane manufacturing to 80° C.

3. A glass plate was used as a forming device. The glass plate was placed on a hot plate, and the temperature of the hot plate was regulated to bring the temperature of the surface of the glass plate to 30° C. In order to adjust the thickness of the membrane in membrane manufacturing, tapes were placed on one end and another end of the glass plate.

4. The stock solution for membrane manufacturing at 80° C. was dropped onto the one end of the glass plate. The stock solution for membrane manufacturing on the glass plate was spread evenly by a glass rod.

5. In the atmosphere, the above was left for one minute under a room-temperature (25° C.) environment.

6. The glass plate coated with the stock solution for membrane manufacturing was immersed into a coagulation bath containing warm water of 30° C.

7. The additive and the solvent in the stock solution for membrane manufacturing were diffused in the coagulation bath, and the resin component coagulated to yield a semipermeable membrane. When 10 minutes had passed since the onset of the immersion, the semipermeable membrane was peeled off the glass plate in the water.

8. The semipermeable membrane was sandwiched by two rectangular metal laths in the water, and the metal laths were fixed at two positions on each side to fix the four sides of the semipermeable membrane.

9. When 15 minutes had passed since the onset of the immersion, the semipermeable membrane was moved into warm water of 30° C. and left immersed in the water overnight.

10. The semipermeable membrane was removed from the water. The semipermeable membrane was moved into a mixed solution of acetone and water. The volume ratio of acetone and water was 8/2, and the temperature was 25° C. The semipermeable membrane was immersed in the stated mixed solution for 15 minutes.

11. The semipermeable membrane was removed from the mixed solution. The semipermeable membrane was moved into acetone and immersed in acetone of 25° C. for 15 minutes.

12. The semipermeable membrane was removed from acetone and left standing for one hour under a room-temperature (25° C.) environment in the atmosphere.

13. The semipermeable membrane was dried for one hour in a drier set to 40° C., and thus the semipermeable membrane measuring 150 mm on a long side and 120 mm on a short side and having a thickness of 100 µm was obtained.

In Example 2, the temperature of the stock solution for membrane manufacturing indicated in the above 2 was changed to 60° C.

In Example 3, the temperature of the coagulation bath indicated in the above 6 was changed to 60° C.

In Example 4, the mass ratio of EVOH-1, DMSO, and PEO indicated in the above 1 was changed to 20:12:68.

In Example 5, the mass ratio of EVOH-1, DMSO, and PEO indicated in the above 1 was changed to 10:7.5:82.5.

In Example 6, the additive indicated in the above 1 was changed to polyethylene glycol (PEG, the molecular weight was approximately 20,000).

In Example 7, EVOH-1 indicated in the above 1 was changed to an ethylene-vinylalcohol-based copolymer (manufactured by KURARAY CO., LTD., Kuraray EVAL (registered trademark) F101B, the content by percentage of an ethylene structural unit was 32 mol %, the degree of saponification was 98 mol %, EVOH-2 in the present specification). In addition, the composition was changed as indicated in Table 1.

In Example 8, EVOH-1 indicated in the above 1 was changed to a polysulfone-based polymer (PS) (manufactured by Amoco Corporation, UDEL P-1700), the additive was changed to polyethylene oxide (PEO, the molecular weight was 60,000), and the solvent was changed to dimethylacetamide (DMAc). In addition, the composition was changed as indicated in Table 1.

In Example 9, EVOH-1 indicated in the above 1 was changed to an ethylene-vinylalcohol-based copolymer (the content by percentage of an ethylene structural unit was 9 mol %, the degree of saponification was 98 mol %, EVOH-3 in the present specification). In addition, the composition was changed as indicated in Table 1.

In Comparative Example 1, the mass ratio of EVOH-1, DMSO, and PEO indicated in the above 1 was changed to 15:85:0.

In Comparative Example 2, the mass ratio of EVOH-1, DMSO, and PEO indicated in the above 1 was changed to 10:20:30.

In Comparative Example 3, the semipermeable membrane was fabricated in accordance with Example 3 in Japanese Unexamined Patent Application Publication No. 2001-314736. In other words, the additive indicated in the above 1 was changed to water and lithium chloride. In addition, the composition was changed as indicated in Table 1.

In Comparative Example 4, the semipermeable membrane was fabricated in accordance with Example 4 in Japanese Unexamined Patent Application Publication No. 2001-314736. In other words, EVOH-1 indicated in the above 1 was changed to a polysulfone-based polymer (PS) (manufactured by Amoco Corporation, UDEL P-1700), the additive was changed to polyethylene glycol (PEG, the molecular weight was 600) and polyvinylpyrrolidone (PVP) (manufactured by BASF Corporation, K-90), and the solvent was changed to dimethylacetamide (DMAc). In addition, the composition was changed as indicated in Table 1.

In Comparative Example 5, the height of the tapes for adjusting the thickness in the operation in the above 3 was adjusted, and a semipermeable membrane having a thickness of 300 μm was obtained.

Complement Level-HA Test Wako available from Wako Pure Chemical Industries Ltd. and Immunoturbidimetric Test CH50 Auto (KW) available from Japan BCG Laboratory.

TABLE 1

| | | | Membrane Manufacturing Condition | | |
|---|---|---|---|---|---|
| | Material | Additive | Composition Material/Additive/Solvent | Stock Solution Temperature ° C. | Coagulation Bath Temperature ° C. |
| Example 1 | EVOH-1 | PEO | EVOH/PEO/DMSO 15/10/75 | 30 | 30 |
| Example 2 | EVOH-1 | PEO | EVOH/PEO/DMSO 15/10/75 | 60 | 30 |
| Example 3 | EVOH-1 | PEO | EVOH/PEO/DMSO 15/10/75 | 30 | 60 |
| Example 4 | EVOH-1 | PEO | EVOH/PEO/DMSO 20/12/68 | 30 | 30 |
| Example 5 | EVOH-1 | PEO | EVOH/PEO/DMSO 10/7.5/82.5 | 30 | 30 |
| Example 6 | EVOH-1 | PEG 20,000 | EVOH/PEG/DMSO 15/10/75 | 30 | 30 |
| Example 7 | EVOH-2 | PEO | EVOH/PEO/DMSO 20/10/70 | 30 | 30 |
| Example 8 | PS | PEO | PS/PEO/DMAc 18/10/72 | 30 | 30 |
| Example 9 | EVOH-3 | PEO | EVOH/PEO/DMSO 25/10/65 | 30 | 30 |
| Comparative Example 1 | EVOH-1 | — | EVOH/DMSO 15/85 | 30 | 30 |
| Comparative Example 2 | EVOH-1 | PEO | EVOH/PEO/DMSO 5/25/70 | 30 | 30 |
| Comparative Example 3 | EVOH-1 | water and LiCl | EVOH/water/LiCl/DMSO 15/4/2/79 | 30 | 30 |
| Comparative Example 4 | PS | PEG600 and PVP | PS/PEG/PVP/DMAc 18/21.6/1/59.4 | 30 | 30 |
| Comparative Example 5 | EVOH-1 | PEO | EVOH/PEO/DMSO 15/10/75 | 30 | 30 |

| | Property of Permeable Membrane | | | | | | |
|---|---|---|---|---|---|---|---|
| | Mean Pore Size nm | Mean Membrane Thickness μm | Water Permeability L/(m² · hour) | Complement Level Decrease Rate % | Complement Activation Rate % | Albumin Adsorption Amount μg/cm² | Albumin Permeation Rate % |
| Example 1 | 450 | 100 | 2500 | 20 | 23 | 4.1 | 55 |
| Example 2 | 520 | 100 | 3200 | 20 | 24 | 4.0 | 68 |
| Example 3 | 600 | 100 | 9000 | 21 | 22 | 4.2 | 43 |
| Example 4 | 420 | 100 | 2300 | 21 | 25 | 4.2 | 52 |
| Example 5 | 510 | 100 | 8600 | 20 | 22 | 3.9 | 71 |
| Example 6 | 370 | 100 | 1200 | 20 | 24 | 3.8 | 35 |
| Example 7 | 430 | 100 | 2200 | 21 | 24 | 4.2 | 53 |
| Example 8 | 340 | 100 | 1900 | 24 | 26 | 6.9 | 47 |
| Example 9 | 320 | 100 | 1600 | 32 | 40 | 6.9 | 34 |
| Comparative Example 1 | 15 | 100 | 120 | 21 | 25 | 3.3 | 0 |
| Comparative Example 2 | The membrane was nonuniform and fragile, thus the measurement was unavailable and was not carried out. | | | | | | |
| Comparative Example 3 | 10 | 100 | 180 | 21 | 24 | 3.5 | 0 |
| Comparative Example 4 | 8 | 100 | 200 | 22 | 27 | 7.1 | 0 |
| Comparative Example 5 | 420 | 300 | 750 | 23 | 24 | 4.2 | 14 |

With the use of the above semipermeable membranes, the serum complement level, the activity of individual complements, and the adsorptivity of albumin were measured. The measuring methods are illustrated below.

[Method A: Measurement of Serum Complement Level (CH50)]

The serum complement level (CH50) can be measured with the use of a commercially available measurement reagent. Examples of the measurement reagent include The rate of decrease in the serum complement level (CH50) in the fresh human serum (complement level decrease rate) by the semipermeable membranes according to Examples 1 to 8 and Comparative Examples 1 and 3 to 5 was no higher than 25%. Thus, the surfaces of these semipermeable membranes were evaluated to be less likely to activate a complement.

[Method B: Measurement of Activity of Individual Complements]

The activity of individual complements was measured with the use of Human OPtEIA ELISA Set C3a (Cat. No 550499) available from BD Biosciences. In this measurement, what was to be measured was a protein C3a to be eliminated from the complements. C3a can be used effectively as an index of an onset of activation of a complement system.

1. The semipermeable membranes according to the examples and the comparative examples were each cut into a piece measuring 10 mm on each side with the thickness unchanged.

2. Each semipermeable membrane piece was immersed in ethanol of 25° C. for no less than 30 minutes, and the air bubbles in the pores in the semipermeable membrane were removed. Thereafter, the semipermeable membrane was washed with PBS(−). The term "PBS(−)" indicates PBS (phosphate buffered saline) free of magnesium and calcium.

3. Each semipermeable membrane piece was placed into a test tube along with 2.0 mL of a fresh human serum. The ratio of the semipermeable membrane to the serum (the surface area of the semipermeable membrane/the volume of the serum) was set to 1 ($cm^2$/mL) (the area on the thickness portion was small and was thus ignored). The test tube was used with its inner surface having been blocked with albumin in advance.

4. For negative control, a fresh human serum with no semipermeable membrane piece placed therein was placed into a test tube in a similar manner. For positive control, a fresh human serum with no semipermeable membrane piece placed therein but with 20 mg of zymosan (Z4350-1G manufactured by SIGMA) added therein was placed into a test tube. These test tubes were heated while being stirred and incubated for 90 minutes at 37° C.

5. The semipermeable membrane pieces were pulled out from test tubes. The activity of the complements in each serum was measured. The measurement was carried out with the use of the ELISA kit with Catalog No. 550499 available from BD Biosciences. The measurement was carried out in accordance with the protocol included in the stated kit.

6. The activation rate was obtained through the following formula. The value (mass of C3a) of the activity of the complements in the fresh human serums with the semipermeable membrane pieces according to the examples and the comparative examples is designated by Xn. The value of the activity in the negative control is designated by Xmin. The value of the activity in the positive control is designated by Xmax. The activation rate can be calculated through the following formula.

Activation rate (%)={($Xn-Xmin$)/($Xmax-Xmin$)}×100

The activation rate of the individual complements in the serums by the semipermeable membranes according to Examples 1 to 8 and Comparative Examples 1 and 3 to 5, or in other words, the activation rate of C3a (complement activation rate) was no higher than 30%. Thus, the surfaces of these semipermeable membranes were evaluated to be less likely to activate the complements.

[Measurement of Adsorptivity of Albumin]

1. The semipermeable membranes according to the examples and the comparative examples were each cut into a piece measuring 10 mm on each side with the thickness unchanged. Each semipermeable membrane piece was immersed in ethanol of 25° C. for no less than 30 minutes. Thereafter, the semipermeable membrane piece was washed with PBS(−).

2. Each membrane piece was immersed in a human albumin (A1653-10G manufactured by SIGMA) solution. The concentration of the albumin solution was 0.1% (1 mg/mL), the temperature was 30° C., and the volume of the solution was 2.4 mL. The immersion was performed for 90 minutes.

3. After the immersion, the semipermeable membrane piece was removed from the solution.

4. The concentration of albumin in the remaining solution was measured to calculate the amount of albumin adsorbed onto the semipermeable membrane piece. The measurement was carried out through an ELISA technique. The measurement through the ELISA technique was carried out with the use of Human Albumin ELISA Quantitation Set (Bethyl Laboratories, Inc.).

The amount of albumin adsorbed onto the semipermeable membranes according to Examples 1 to 9 and Comparative Examples 1 and 3 to 5 was no higher than 10 μg/$cm^2$. Thus, the surfaces of these semipermeable membranes were evaluated to be less likely to adsorb proteins.

[Measurement of Water Permeability]

1. The semipermeable membranes according to the examples and the comparative examples were each cut into a piece measuring 3 cm on each side with the thickness unchanged.

2. Each membrane piece was immersed in ethanol of 25° C. for no less than 30 minutes.

3. Thereafter, the membrane piece was immersed in distilled water of 30° C. for no less than 30 minutes.

4. The membrane was mounted onto a graduated filter holder (FILTER HOLDER: manufactured by ADVANTEC, 25 mm, the filter area was 3.14 $cm^2$). The filter holder is constituted by a lower component, a spacer, an upper component, and a clip. The upper component is a component that functions as a support for an outer frame and a semipermeable membrane. The spacer was placed on the lower component, the semipermeable membrane was placed on the spacer, and the upper component was placed on the semipermeable membrane. The upper component and the lower component were pinched by the clip to be fixed together. The lower component was connected to a suction bottle.

5. Eleven milliliters of distilled water was placed into the upper component of the graduated filter holder.

6. The graduated filter holder was connected to an aspirator, and the aspirator was then put into operation to reduce the pressure in the lower component where the semipermeable membrane is not in contact with the distilled water. At this point, the water temperature was 25° C., and the magnitude of the negative pressure was 3±0.2 kPa.

7. The time it took for the volume of the distilled water in the upper component to change from 10 mL to 5 mL was recorded. In a case in which the stated time was no less than 10 minutes, the amount of filtered water in 10 minutes after starting to reduce the pressure was recorded.

8. The water permeability of the semipermeable membrane is expressed by the amount of permeated water {L/($m^2$·hour)} per effective unit area of the membrane mounted on the filter holder and per unit time. In each of the examples and the comparative examples, four semipermeable membranes were prepared, and the measurement was carried out four times. The mean value thereof was regarded as a representative value to serve as the value of the water permeability.

In the membrane according to Example 1, the mean of four instances of measurement on the time it took for the volume of the distilled water to change from 10 mL to 5 mL was 22.9 seconds. Thus, the amount of permeated water was 5 mL/(3.14 cm$^2$·22.9 sec), or in other words, the stated amount was 2,500 L/(m$^2$·hour) upon 5/4 rounding of the first digit.

The water permeability of each of the semipermeable membranes according to the examples and the comparative examples is as indicated in Table 1, and the water permeability of the semipermeable membranes according to Examples 1 to 9 was no lower than 1,000 L/(m$^2$·hour). Thus, the semipermeable membranes were evaluated to have high water permeability.

[Measurement of Permeation Rate of Albumin]

1. The semipermeable membranes according to the examples and the comparative examples were each cut into a piece measuring 25 mm on a short side and 40 mm on a long side with the thickness unchanged. Each semipermeable membrane piece was immersed in ethanol of 25° C. for no less than 30 minutes and was then washed with PBS(−).

2. The long side portions were folded together, and the two long side portions were fused and bonded by a heat sealer to fabricate a bag-like member with the short sides left open.

3. The stated member was charged with 200 μL of a 20 mg/L human albumin solution, and the short side portions were each sealed by the heat sealer to fabricate a bag.

4. The bag containing the albumin solution was immersed in 10 mL of Hanks' buffer solution in a 15-mL tube and shaken for 30 minutes at 37° C.

5. After one hour, the Hanks' buffer solution outside the bag was sampled.

6. The concentration of albumin in the sampled Hanks' buffer solution was measured through an ELISA technique. The measurement through the ELISA technique was carried out with the use of Human Albumin ELISA Quantitation Set (Bethyl Laboratories, Inc.).

7. The permeation rate was obtained through the following formula. The amount of permeated albumin that has moved from the bag to the Hanks' buffer solution is designated by Xn. The amount of albumin placed into the bag is designated by Xmax. Specifically, Xmax was 20 mg/L×200 μL, or 400 ng.

Permeation rate (%)=$Xn/X$max×100

The permeation rate of albumin in the semipermeable membranes according to Examples 1 to 9 was no lower than 30%. Thus, the semipermeable membranes were evaluated to have high substance permeability for proteins or the like.

[Measurement of Membrane Thickness]

The membrane thickness was measured with a membrane thickness gauge, and the mean of the measured values at four corners of each manufactured semipermeable membrane was regarded as the membrane thickness of that semipermeable membrane. The membrane thickness of each of the membranes according to the examples and the comparative examples is indicated in Table 1.

[Measurement of Mean Pore Size]

The pore sizes of the pores in the semipermeable membranes were measured by observing the surfaces of the semipermeable membranes. One surface of each semipermeable membrane was photographed by a scanning electron microscope at a magnification rate of 2,000 times. After photographing, 30 pores, or air gaps, were selected randomly, and the diameter of each air gap was measured. The mean of the measured values was regarded as the mean pore size of the pores in the semipermeable membrane.

[Evaluation]

As described above, the surfaces of the semipermeable membranes according to the examples were less likely to adsorb albumin, or proteins. Accordingly, it was suggested that the semipermeable membranes according to the examples had good biological compatibility. In addition, the surfaces of the semipermeable membranes according to the examples were less likely to activate the complements. Accordingly, it was suggested that the membranes according to the examples suppressed a decrease over time in the substance permeability of the semipermeable membranes in an organism. In addition, it was found from the measurement of the permeation rate of albumin that the semipermeable membranes according to the examples had pores that were large enough to allow the nutrients or the secreted substances to permeate therethrough. Accordingly, it was suggested that the semipermeable membranes according to the present disclosure exceled in the substance permeability. In addition, the semipermeable membranes according to the present disclosure exceled in the water permeability.

In contrast, the semipermeable membranes according to Comparative Examples 1, 3, and 4 had a small mean pore size and were inferior in terms of the water permeability and the permeability of nutrients and secreted substances. In addition, the semipermeable membrane according to Comparative Example 2 did not result in a uniform membrane and was inferior in terms of durability. The semipermeable membrane according to Comparative Example 2 is characterized by a low proportion of resin in the stock solution for membrane manufacturing.

The semipermeable membrane according to Comparative Example 5 had a low permeation rate of albumin. This is because, although the semipermeable membrane according to Comparative Example 5 was composed of the materials similar to those of the semipermeable membrane according to Example 1, the semipermeable membrane according to Comparative Example 5 was thicker than the semipermeable membrane according to Example 1.

The semipermeable membrane according to Example 9 activated the complements more easily than did the semipermeable membranes according to Examples 1 to 8. This is because the semipermeable membrane according to Example 9 adsorbed albumin relatively easily since an ethylene-vinylalcohol-based copolymer having a low content of an ethylene structural unit was used in the semipermeable membrane according to Example 9.

On the basis of the above, the semipermeable membrane according to the present disclosure illustrated in Examples 1 to 9 has high substance permeability as well as tolerance against a decrease over time in the substance permeability of the semipermeable membrane in an organism. Accordingly, the semipermeable membrane according to the present disclosure has good biological compatibility.

This application claims priority to Japanese Patent Application No. 2016-007721, filed on Jan. 19, 2016, the entire disclosure of which is incorporated herein.

REFERENCE SIGNS LIST 10 semipermeable membrane, 11 base material, 12 cell, 15 nutrient, 16 secreted substance, 18 leucocyte

The invention claimed is:

1. A semipermeable membrane, comprising:
a resin,
wherein:
a permeation rate of albumin is no lower than 30%; and
an albumin adsorption amount obtained when the semipermeable membrane measuring 1 cm on each side is immersed in a 0.1% albumin solution for 90 minutes is no greater than 10 μg/cm$^2$,
wherein a water permeation amount obtained when water is drawn through the semipermeable membrane at a negative pressure of 3±0.2 kPa is no smaller than 1,000 L/(m$^2$·hour).

2. The semipermeable membrane according to claim 1, wherein a decrease in a complement level (CH50) in a serum by the semipermeable membrane, when the semipermeable membrane and the serum are brought into contact, is no more than 25%.

3. The semipermeable membrane according to claim 1, wherein:
an increase in an activity of a complement in a serum by the semipermeable membrane, when the semipermeable membrane and the serum are brought into contact, is no more than 30%; and
the increase in the activity is calculated on the basis of an amount of one or more complements among C1, C2, C3, C4, C5, C6, C7, C8, and C9, an amount of a protein produced as the complements are degraded, and a measured amount of one or more of complexes of the complements.

4. The semipermeable membrane according to claim 1, wherein the semipermeable membrane has a thickness of no less than 50 μm nor more than 200 μm.

5. The semipermeable membrane according to claim 1, wherein a mean pore size in at least one surface is no less than 0.5 μm nor more than 3 μm.

6. The semipermeable membrane according to claim 1, wherein:
the resin is an ethylene-vinylalcohol-based copolymer; and
the semipermeable membrane comprises the ethylene-vinylalcohol-based copolymer at no less than 50 mass %.

7. The semipermeable membrane according to claim 1, wherein the semipermeable membrane is adapted to function as a semipermeable membrane for isolating a cell from an external environment.

8. A bag, consisting of the semipermeable membrane according to claim 1, comprising:
a semipermeable membrane comprising a resin,
a base material, and
cells;
wherein the semipermeable membrane fully encloses the base material and the cells.

9. A bag made from the semipermeable membrane according to claim 1, wherein the semipermeable membrane is sealed and defines an exterior layer surrounding an enclosed space.

10. The bag of claim 9, wherein the enclosed space contains a liquid comprising albumin.

11. A bag having a layer defining a fully enclosed space, wherein the layer consists of the semipermeable membrane according to claim 1, and wherein the enclosed space comprises a base material and cells.

12. The bag of claim 8, wherein the semipermeable membrane has a mean pore size in at least one surface of no less than 0.5 μm nor more than 3 μm.

13. The bag of claim 9, wherein the semipermeable membrane has a mean pore size in at least one surface of no less than 0.5 μm nor more than 3 μm.

14. The bag of claim 11, wherein the semipermeable membrane has a mean pore size in at least one surface of no less than 0.5 μm nor more than 3 μm.

* * * * *